United States Patent [19]

Halka

[11] Patent Number: Plant 5,687

[45] Date of Patent: Mar. 11, 1986

[54] ZELKOVA TREE

[75] Inventor: Chester J. Halka, Englishtown, N.J.

[73] Assignee: J. Frank Schmidt & Son Co., Boring, Oreg.

[21] Appl. No.: 629,117

[22] Filed: Jul. 9, 1984

[51] Int. Cl.[4] ..... A01H 5/12
[52] U.S. Cl. ..... Plt./51
[58] Field of Search ..... Plt./51

[56] References Cited

U.S. PATENT DOCUMENTS

P.P. 5,080 8/1983 Flemer ..... Plt./51

*Primary Examiner*—Robert E. Bagwill
*Attorney, Agent, or Firm*—Klarquist, Sparkman, Campbell, Leigh & Whinston

[57] ABSTRACT

A novel Japanese zelkova tree characterized by its rapid growth rate, large foliage, long arching branches, yellow autumn color, and somewhat earlier autumn color changes and defoliation.

3 Drawing Figures

The present invention relates to a new and distinct variety of Japanese zelkova tree of the species botanically known as *Zelkova serrata*. I have named my new variety "Halka". I discovered my new variety as a seedling mutation of unknown parentage which was being grown in a cultivated area of my nursery in Englishtown, N.J.

While caring for this nursery, my attention was attracted to the new seedling because of it's rapid growth. This seedling continued to show exceptional vigor and grew into an unusually tall narrow tree with very long, gracefully arching branches.

Close observations of the new seedling and continued observations of progeny thereof subsequently asexually propagated under my direction by budding on Japanese zelkova seedling understock, has confirmed that the unique characteristics of my new variety is a result of a seedling variation. I am therefore convinced that my new tree represents a new and improved variety of *Zelkova serrata*, as particularly evidenced by the following unique combination of characteristics, which have proven firmly fixed, are outstanding therein, and which distinguish it from other varieties of this species:

1. An extremely rapid, vigorous and upright habit of growth;
2. Large foliage;
3. Long arching branches;
4. Foliage which assumes a yellow autumn color, instead of orange and red tones; and
5. Somewhat early Fall changes.

The accompanying photographs depict the color of the foliage of my new variety as nearly true as is reasonably possible to make the same in a color illustration of this character.

FIG. 1 is a color photograph of a tree of the present invention taken in early Fall of 1983;

FIG. 2 is a color photograph of leaves of the tree of FIG. 1, showing the color of the leaves prior to their autumn color change; and FIG. 3 is a color photograph of leaves of the tree of FIG. 1, showing their autumn colors.

One of the primary distinguishing features of my new tree over other trees of this species is it's extremely rapid rate of growth. As a specific example, the height of my new variety has been compared with the height of both the Village Green and seedling Japanese zelkova trees. In one specific comparison of twenty-five one year old trees of each variety growing in the same locale, my new variety, averaged 317 cm in height, the Village Green variety averaged 248 cm in height and seedling Japanese zelkova trees averaged 159 cm in height. In an earlier comparison of a different group of twenty trees of each variety, each one year old and growing in the same locale, the height of trees of my new variety averaged 277 cm, the height of trees of the Village Green variety averaged 213 cm, and the height of the seedling trees averaged 118 cm. Thus, consistently, my new Japanese zelkova variety is a faster growing tree.

In addition, observations of the branches of my new variety in comparison with the branches of the Village Green and seedling varieties of zelkova trees have been made. These comparisons have convinced me that my new variety of tree on the average has longer branches than these other varieties. In addition, on the average, the leaves of my new variety are somewhat larger than the leaves of both the Village Green and seedling zelkova trees. This feature contributes to my trees' distinctive appearance.

Also, in contrast to the orange/red autumn color tones of the foliage of the Village Green and seedling Japanese zelkova trees, the foliage of my new variety turns more to a yellow autumn color. In addition, the leaves of my new variety change from green to their autumn color and fall from the trees approximately two weeks earlier than similar changes in the Village Green zelkova trees, and one week earlier than similar changes in seedling Japanese zelkova trees.

Otherwise, so far as I have observed at this time, my new variety is generally typical of the species.

The following is a detailed description of my new variety of "Halka" *Zelkova serrata* tree, with color terminology in accordance with The Royal Horticultural Society Color Chart (hereinafter R.H.S.), published by The Royal Horticultural Society of London.

Parentage: A seedling mutation of unknown parentage.
Propagation: Holds to distinguishing characteristics through succeeding propagation by budding.
Localities where grown and observed: Englishtown, N.J. and Boring, Oreg.
Tree: Upright, healthy, very vigourous; rapid growing.

Foliage:

*Leaves.*—Alternate, simple.

*Leaf size.*—Length-typically about 13 cm; Breadth typically about 7 cm.

*Shape.*—Ovate to oblong ovate.

*Margin.*—Strongly serrated, teeth rounded with mucronate tips.

*Tip.*—Acuminate.

*Base.*—Truncate to cordate.

*Surface.*—Rough textured above, glabrous underside.

*Color.*—As described above and more specifically: The leaf summer color is a green color (similar to R.H.S. 137A). In the Fall, the leaves turn to a yellow autumn color (similar to R.H.S. 21B).

Buds: Round with brown, imbricate scales.

Branches: Long, slender and arching.

Fall Changes: As described above, somewhat earlier than similar changes in other varieties of Japanese zelkova trees.

I claim:

1. A new and distinct variety of Japanese zelkova tree, substantially as herein shown and described, characterized particularly as to novelty by its rapid rate of growth, large foliage, long arching branches, yellow autumn color of its foliage and autumn changes which occur somewhat earlier than similar changes in other Japanese zelkova varieties.

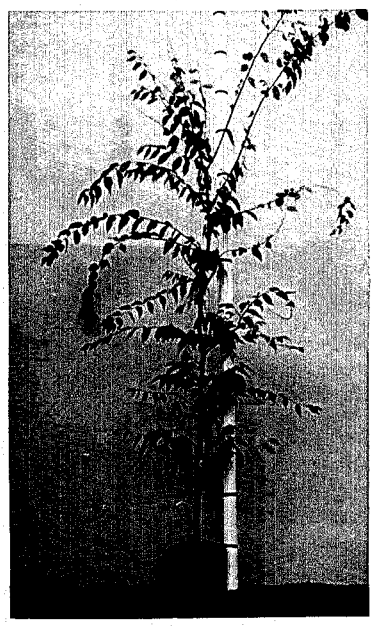
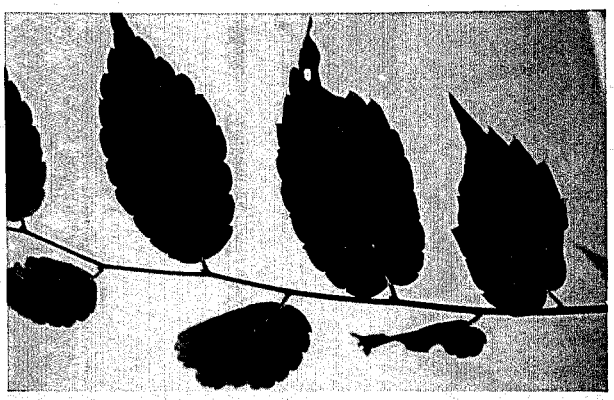
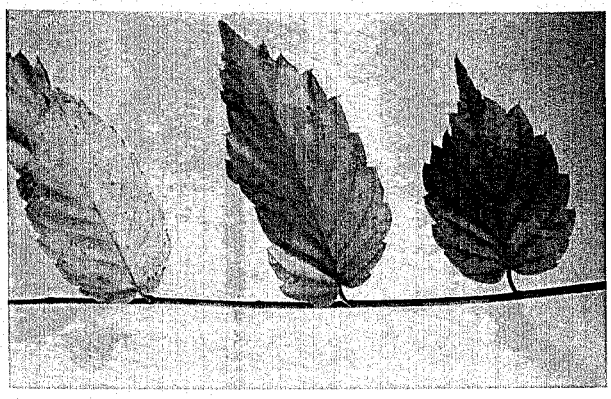

* * * * *